United States Patent
Parks et al.

(10) Patent No.: US 8,451,444 B2
(45) Date of Patent: May 28, 2013

(54) OPTICAL BACKSCATTER PROBE FOR SENSING PARTICULATE IN A COMBUSTION GAS STREAM

(75) Inventors: James E. Parks, Knoxville, TN (US); William P. Partridge, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 416 days.

(21) Appl. No.: 12/491,781

(22) Filed: Jun. 25, 2009

(65) Prior Publication Data

US 2010/0328663 A1  Dec. 30, 2010

(51) Int. Cl.
*G01N 21/00* (2006.01)
*G01N 21/53* (2006.01)

(52) U.S. Cl.
CPC ..................... *G01N 21/53* (2013.01)
USPC .......................................... 356/338

(58) Field of Classification Search
USPC .......................... 356/432, 436–442
See application file for complete search history.

(56) References Cited

U.S. PATENT DOCUMENTS

| | | | |
|---|---|---|---|
| 4,361,028 A | 11/1982 | Kamiya et al. | |
| 4,747,297 A | 5/1988 | Okayama et al. | |
| 5,009,064 A | 4/1991 | Grob et al. | |
| 5,110,747 A | 5/1992 | Pataschnick et al. | |
| 5,921,226 A * | 7/1999 | Toyohara et al. | 123/674 |
| 5,984,998 A * | 11/1999 | Ottesen et al. | 75/375 |
| 6,011,622 A * | 1/2000 | Fishkin et al. | 356/339 |
| 6,435,019 B1 * | 8/2002 | Vojtisek-Lom | 73/114.69 |
| 6,700,662 B2 | 3/2004 | Gupta et al. | |
| 2006/0177937 A1 * | 8/2006 | Kurabayashi et al. | 436/63 |
| 2007/0296971 A1 * | 12/2007 | Larsen et al. | 356/338 |

OTHER PUBLICATIONS

Fierro, Marian. "Particulate Matter" Mar. 3, 2000.*
Arlon J. Hunt & Donald R. Huffman; A New Polarization-Modulated Light Scattering Instrument; Rev. Sci. Instrum., vol. 44, No. 12, Dec. 1973; Copyright 1973 by the American Institute of Physics; Department of Physics, University of Arizona, Tuscon, Arizona; Sep. 1973 (10 pages).
A.J. Hunt, M.S. Quinby & I. G. Shepherd; Diesel Exhaust Particle Characterization by Polarized Light Scattering; SAE Technical Paper Series 982629; International Fall Fuels & Lubricants Meeting & Exposition; San Francisco, California Oct. 19-22, 1998 (10 pages).
Peter O. Witze, Shean P. Huff, John M. Storey & Brian H. West; Time-Resolved Laser-Induced Incandescence Measurements of Particulate Emissions During Enrichment for Diesel Lean NOx Trap Regeneration; SAE Technical Paper Series 2005-01-0186; 2005 SAE World Congress; Detroit, Michigan; Apr. 11-14, 2005 (12 pages). Reprinted from Emissions Measurement & Testing 2005 (SP-1941).

* cited by examiner

*Primary Examiner* — Taara S Pajoohi Gomez
(74) *Attorney, Agent, or Firm* — Luedeka Neely Group, P.C.

(57) ABSTRACT

A system for sensing particulate in a combustion gas stream is disclosed. The system transmits light into a combustion gas stream, and thereafter detects a portion of the transmitted light as scattered light in an amount corresponding to the amount of particulates in the emissions. Purge gas may be supplied adjacent the light supply and the detector to reduce particles in the emissions from coating or otherwise compromising the transmission of light into the emissions and recovery of scattered light from the emissions.

27 Claims, 3 Drawing Sheets

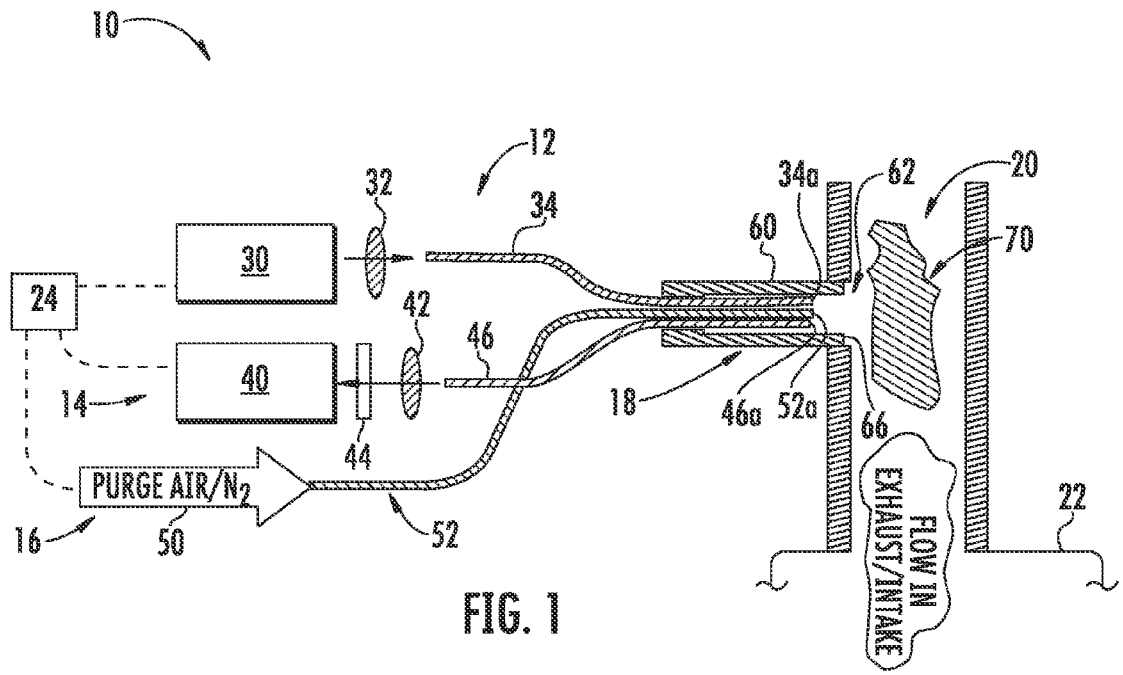
FIG. 1
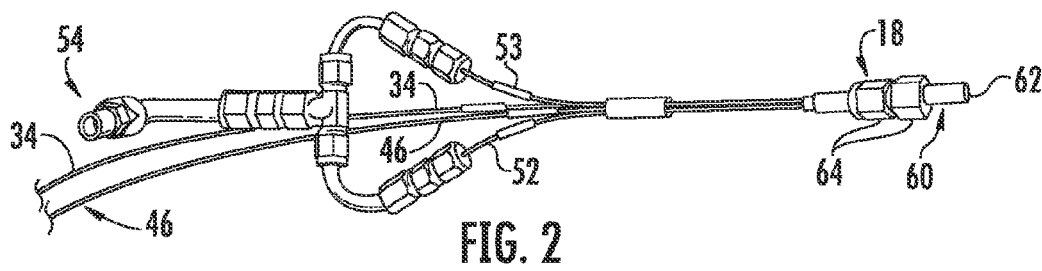
FIG. 2
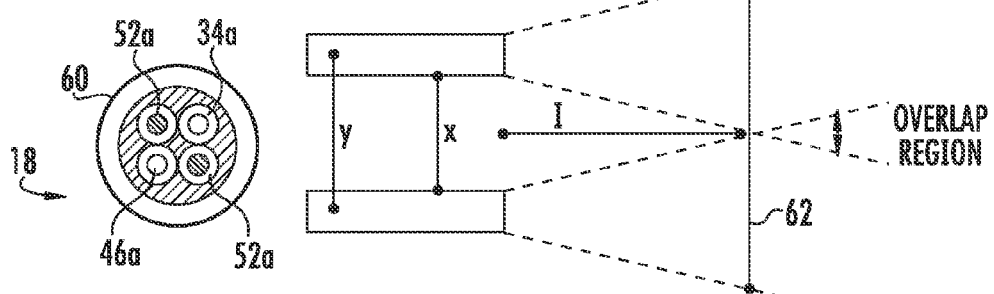
FIG. 3
FIG. 4

OPTICAL BACKSCATTER PROBE FOR SENSING PARTICULATE IN A COMBUSTION GAS STREAM

GOVERNMENT RIGHTS

This invention was made with government support under Contract No. DE-AC05-00OR22725 awarded by the U.S. Department of Energy. The government has certain rights in the invention.

FIELD

This disclosure relates to the field of measurement of particulate matter in gas streams. More particularly, this disclosure relates to optical probes for measuring particular emissions from combustion processes.

BACKGROUND

Reduction of vehicle emissions is an on-going objective of the automotive industry. Information concerning the emissions of an engine is desired by automotive designers in designing multi-cylinder engines. In addition, information concerning the emissions of an engine in operation, such as in a passenger vehicle, is desirable for use by on-board systems for minimizing emissions and/or by automotive technicians in diagnosing and repairing engine problems causing undesirably high emissions.

Conventional emissions measurement equipment needs improvement. For example, such equipment is unable to be easily incorporated into hard to access portions of multi-cylinder engines, does not provide suitable information of the emissions of the individual cylinders of a multi-cylinder engine, and/or is too fragile and/or expensive to be utilized in production engines.

Accordingly, a need exists in the art for a system for measuring engine emissions that can readily be incorporated into hard to access portions of an engine, provides information of the emissions of the individual cylinders of a multi-cylinder engine, is economical, and durable.

SUMMARY

The present disclosure provides a system for measuring particulate in the gas emissions of an internal combustion engine. The system supplies light into a location of the engine or associated exhaust system having emissions, and thereafter detects scattered light in an amount corresponding to the amount of particulates in the emissions.

In one embodiment, the system includes a stream of combustion gas containing entrained particulate matter. A light transmission system is provided to transmit light into the combustion gas. The light transmission system includes a source of light and a light transmitter positioned relative to the stream of combustion gas to transmit light into the stream of combustion gas. Transmitted light is scattered by the particulate matter.

A light collection system collects and detects the scattered light. The light collection system includes a light detector and a light collector positioned relative to the stream of combustion gas and the light transmitter for being exposed to transmitted light scattered by the particulate matter and collecting and directing scattered light to the light detector.

A controller is operatively associated with the light transmission system and the light collection system for sending command signals to the source of light and recording signals generated by the detector as a function of time to provide an indication of the amount of particulate matter in the stream of combustion gas.

In another embodiment, the disclosure relates to a method of determining the amount of particulate matter in a stream of combustion gas. The method includes the steps of: providing a stream of combustion gas containing substantially entrained particulate matter; providing a light transmission system, comprising a source of light and a light transmitter positioned relative to the stream of combustion gas, and operating the light transmission system to transmit light into the stream of combustion gas, wherein transmitted light is scattered by the particulate matter; providing a light detector and a light collector positioned relative to the stream of combustion gas and the light transmitter for being exposed to light scattered by the particulate matter and collecting and directing scattered light to the light detector; and monitoring signals generated by the detector as a function of time to provide an indication of the amount of particulate matter in the stream of combustion gas.

BRIEF DESCRIPTION OF THE DRAWINGS

Various advantages are apparent by reference to the detailed description in conjunction with the figures, wherein elements are not to scale so as to more clearly show the details, wherein like reference numbers indicate like elements throughout the several views, and wherein:

FIG. 1 is a schematic diagram of a system for measuring engine emissions according to an embodiment of the disclosure.

FIG. 2 is a plan view of the system of FIG. 1.

FIGS. 3 and 4 show desired positioning of components associated with a probe of the system of FIG. 1.

DETAILED DESCRIPTION

Figure 5:
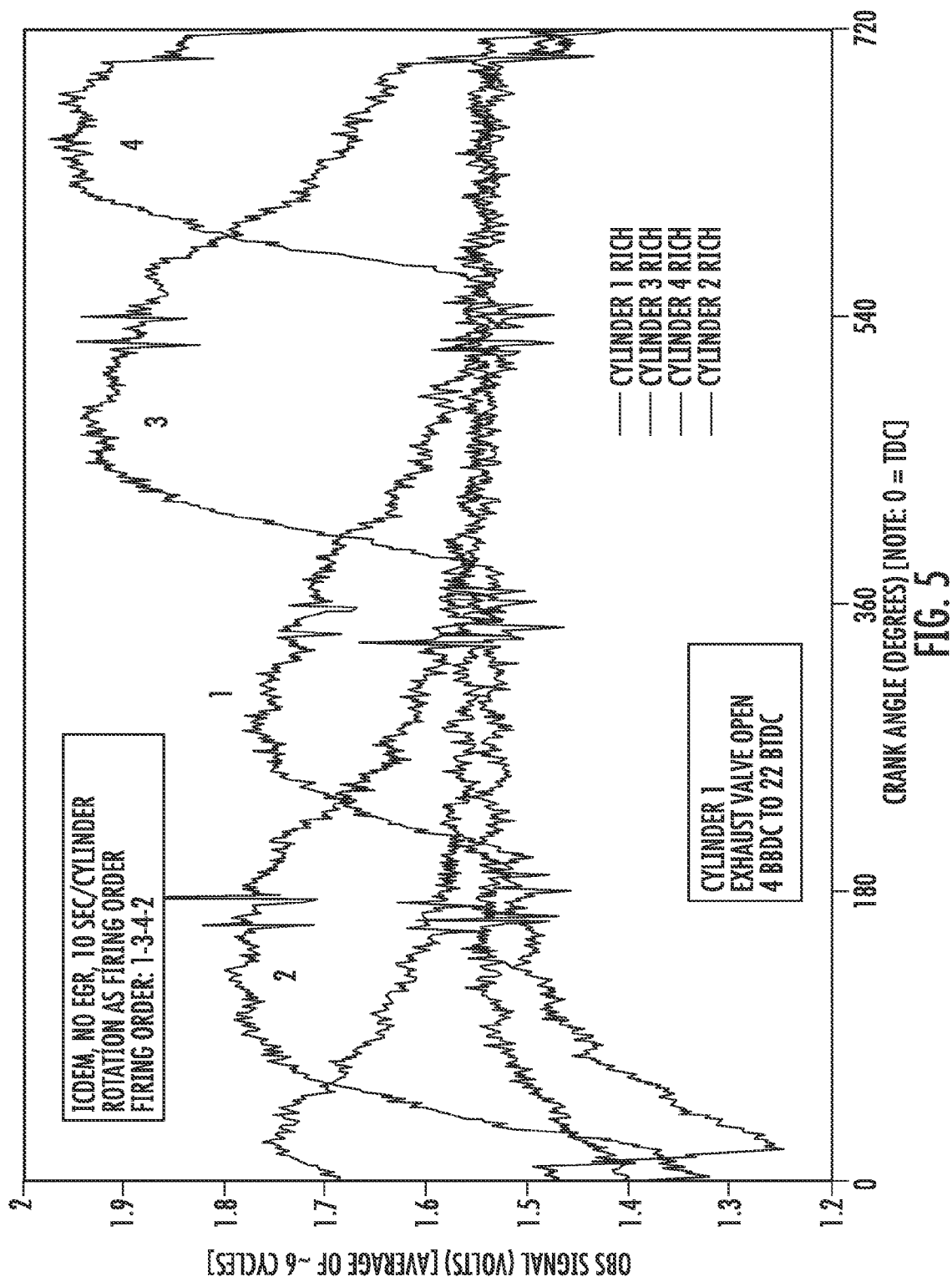
FIG. 5 is a graph showing detection of particulate matter by the system of FIG. 1 in an example operation of the system.

In the following detailed description of embodiments according to the disclosure, reference is made to the accompanying drawings, which form a part hereof, and within which are shown by way of illustration the practice of specific embodiments of a system 10 for measuring emissions of an internal combustion engine. It is to be understood that other embodiments may be utilized, and that structural changes may be made and processes may vary in other embodiments.

In brief overview, the system 10 transmits light into a location of the engine having emissions, and thereafter detects scattered light in an amount corresponding to the amount of particulates in the emissions. That is, if the engine emissions contain a low level of particulate matter, then only a small amount of light will be scattered back to the detector. Conversely, if the engine emissions contain a high level of particulate matter, then a high amount of light will be scattered back to the detector.

To provide longevity to the system 10 and avoid soot buildup on light transmission and detection components, a purge gas is desirably supplied adjacent such components to substantially prevent or inhibit particles in the emissions from coating or otherwise compromising the transmission of light into the emissions and recovery of scattered light from the emissions. The system is compact and integrated into a probe for desirably locating components of the system for interaction with desired engine emissions such as the emissions from a single cylinder or under the body of a vehicle where the exhaust system is located.

The system 10 is configured to provide particulate information of an emission gas of an engine. That is, of a single emission gas stream, such as is associated with a single cylinder of a multi-cylinder engine, or of multiple cylinders, or the exhaust system from the engine which will likely contain emission control devices such as catalysts and diesel particulate filters. Another part of the engine system where particulate measurements are useful is the exhaust gas recirculation (EGR) system that routes exhaust back into the engine intake for the purpose of reducing engine emissions. Particulate measurements are useful on a cylinder-by-cylinder basis for understanding and improving engine balancing and combined emissions and efficiency. Particuate measurements are useful on a cycle-to-cycle basis as well. Furthermore, measurement of particulate upstream and downstream of emission control devices in the exhaust that control particulate emissions is useful for initiating active control events as well as regulatory driven on-board diagnostics to insure correct system operation. The system 10 may be incorporated into a header or other exhaust stream associated with each individual cylinder and/or, in an alternate embodiment, incorporated into a emission gas stream of multiple cylinders, such as occurs in the merged flow of the exhaust pipe downstream of the manifold or header.

With reference to FIG. 1, the system 10 includes a light transmission system 12, a light collection system 14, and a purge gas system 16. A probe 18 is configured for integrating and positioning desired portions of the light transmission system 12, the light collection system 14, and the purge gas system 16 in communication with an emissions source 20 of the internal combustion engine 22. The light transmission system 12, the light collection system 14, and the purge system 16 desirably interface with a controller 24.

The light transmission system 12 is configured to transmit light into the combustion gases of the emissions source 20 and includes a source of light 30, a lens 32, and a fiber optic cable 34. The source of light 30 may be provided as by a laser diode such as a laser diode that emits light at a single wavelength. For the purpose of example, a wavelength of 532 nm is suitable for various applications described herein, but it will be understood that other wavelengths may be more suitable, depending upon the application. The lens 32 may be a collimating lens to align the light rays for travel through the fiber optic cable 34.

The light collection system 14 is configured to collect light scattered by particulate matter entrained in the combustion gas of the emissions source 20 and includes a light detector 40, a lens 42, a filter 44, and a fiber optic cable 46. The light detector 40 may be, for example, a photomultiplier tube detector or a photodiode detector. The lens 42 may be, for example, a collimating lens to align the light rays received from the fiber optic cable 46. The filter 44 may be omitted if desired. In the event the filter 44 is used, the filter 44 may be, for example, a bandpass filter configured to pass only light of the wavelength emitted by the source of light 30. Thus, for use with a 532 nm diode, the filter 44 may be a bandpass filter that only passes 532 nm light. The use of a single wavelength of light in combination with a bandpass filter is desirable to avoid measuring any stray light.

The purge gas system 16 includes a source of pressurized gas 50 and one or more flow conduits 52 for flow of the gas to a desired location of the probe 18. The source of pressurized gas 50 supplies air or an inert gas such as nitrogen at a pressure of about 20 psi at a flow rate of from about 5 to about 10 slpm (standard liters per minute). In this regard, two of the flow conduits 52 may be provided for handling this flow, with each conduit 52 having an internal diameter of about 0.030 inches. A port 54 (FIG. 2) serves to connect the source of gas 50 flowing to the conduits 52.

With reference to FIGS. 1-3, the probe 18 is configured to integrate and position a transmission end 34a of the cable 34 (which transmits light), a collection end 46a of the cable 46 (which receives light), and purge ends 52a of the flow conduits 52 in communication with the emissions source 20 of the internal combustion engine 22. The probe 18 may be provided, for example, by a cylinder 60 provided by a length of ¼ inch internal diameter stainless steel tubing. The fiber optic cables 34 and 46 and the conduits 52 pass through a rear end of the cylinder 60 and terminate at a substantially common longitudinal location of the cylinder 60, slightly interior of an open exit end 62 of the cylinder 60. In this regard, the output ends 52a of the flow conduits 52 may extend just slightly past the ends 34a and 46a of the cables so that the flow of gas therefrom is directed to blow particulate matter away from the ends of the cables to inhibit contact of particulate matter with the ends 34a and 46a of the cables 34 and 46. The cylinder 60 may include a connector 64 for fixedly positioning the cylinder 60 relative to an aperture 66. For example, the aperture 66 may be an aperture located on an exhaust manifold of the engine 22.

With reference to FIGS. 3 and 4, it has been observed that the ends 34a and 46a of the cables 34 and 46 may be located relative to the cylinder 60 and each other to maximize the collection of light scattered by particulate matter in the emissions source 20. For example, it has been observed that the light collection is dependent upon the overlap of the conical "view" of ends 34a and 46a of the cables 34 and 46, as represented in FIG. 4, which depicts the open end 62 of the cylinder 60, with the ends 34a and 46a spaced an inset distance I within the open end 62. The view of end 34a is the cone in which it transmits light and the view of end 46a is the cone from which light is received. Distance X represents the horizontal spacing and distance Y represents the vertical spacing between the ends 34a and 46a, which are arranged relative to one another and the output ends 52a as seen in FIG. 3. For the purpose of example, when the internal diameter of the open end 62 of the conduit 60 is 0.25 inches, the inset distance I may be, for example, about 0.065 inches, the distance X about 0.88 inches, and the distance Y about 0.88 inches.

The emissions source 20 may be any location within the engine 22 or exhaust system of the engine through which emissions travel. In one embodiment, the system 10 is configured to measure particulate matter 70 (FIG. 1) generated by a single cylinder of the engine. Such particulate matter 70 may, for example, contain solid carbonaceous particles, sulfate particles, and the like associated with the operation of an internal combustion engine, and entrained in the combustion exhaust gases. Thus, for such purpose, the emissions source 20 may be directed by a header pipe or a port to an exhaust manifold of the engine.

In another embodiment, the system 10 is configured to measure the particulates in the emissions generated by each cylinder of the engine as a function of time. For this purpose, one of the systems 10 may be incorporated into each flowpath of the header or manifold to measure the particulates generated by each cylinder. Optionally, or in addition, one of the systems 10 may be incorporated into the merged flow pipe of the manifold that receives and mixes the emissions from the cylinders. Other desired locations for installation of one or more of the systems 10 in an engine includes exhaust gas recirculation systems, turbochargers, and virtually any other gas flowpath of the engine that contains emissions or other particulate matter. In this regard, it will be understood that the internal combustion engine 22 may be any internal combustion engine, such as a gasoline engine, ethanol engine, diesel engine, natural gas engine, or the like.

The controller 24 may be any controller suitable for sending command signals to the source of light 30 and recording or otherwise monitoring signals generated by the detector 40. The signals may be monitored, for example, as a function of time, as a function of combustion cycle, as a function of particulate trapping in exhaust, or the like. For the described use with multiple cylinder engines, the controller 24 may be configured for multiplexing multiple signals received from multiple of the systems 10.

The system 10 is suitable for use in a variety of settings and may be used, for example, by automotive designers in designing multi-cylinder engines, or vehicles in on-board systems for minimizing emissions and/or by automotive technicians in diagnosing and repairing engine problems causing undesirably high emissions. The system 10 is compact and easily incorporated into hard to access portions of multi-cylinder engines. The system 10 is suitably economical and durable for implementation into production engines.

The system 10 is furthermore suitable for providing information of the emissions of the individual cylinders of a multi-cylinder engine. Accordingly, for the purpose of example, one of the systems 10 was installed into each of the four exhaust manifolds of a four cylinder internal combustion engine. The engine was operated and each cylinder was sequentially enriched for 10 seconds by adding additional fuel, which resulted in the generation of more particulate matter in the exhaust, the results of which are shown in FIG. 5.

With reference to FIG. 5, the horizontal axis of the graph is relative to time, based on the crank angle, and the vertical axis of the graph is signal received by each of the detectors 40, one for each of the four cylinders of the engine (Cylinders 1, 2, 3, and 4, with the firing order of the engine being 1-3-4-2). The results represent values obtained during six cycles of engine operation. As will be noted, during each 10 second period during which a cylinder was enriched, a corresponding increased signal from the detector was received. Thus, it will be appreciated that the system 10 functioned to provide information of the emissions of the individual cylinders of a multi-cylinder engine.

The system may also be used to monitor emissions in the exhaust system upstream or downstream of an emission control device such as a diesel particulate filter. The system advantageously enables monitoring of the amount of particulate flowing into the device and thereby provides data for active control of the device. The system also serves to provide diagnostics of correct performance of the device by monitoring the downstream particulate level to detect threshold increases in particulate that would signal device malfunction.

Figure 6:
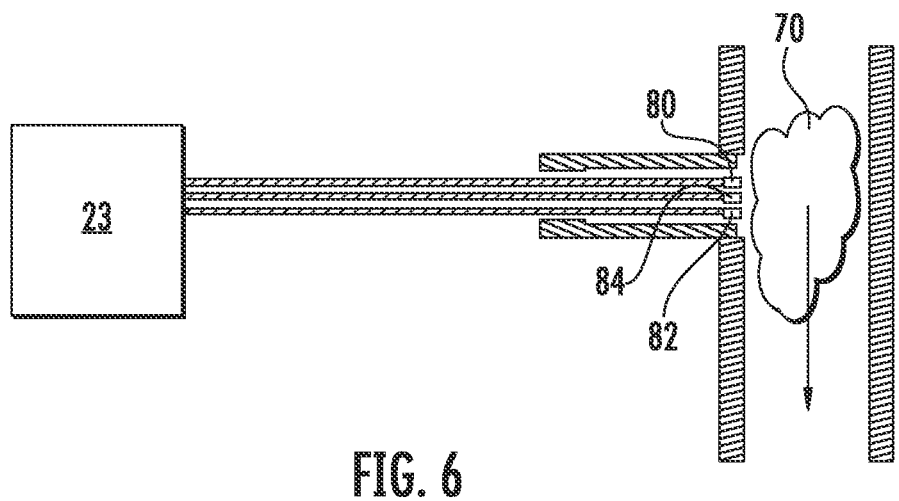
FIG. 6 is a schematic diagram of a system for measuring engine emissions according to an alternative embodiment of the disclosure.

An alternate embodiment is shown in FIG. 6 which is analogous to the embodiment of FIG. 1 except that a photodiode light emitter 80 and a photodiode light detector 82 are mounted to directly transmit light into the exhaust gas stream 70 and directly detect light scattered by the exhaust gas stream 70. The photodiode light emitter 80 may include an integral collimating lens for collimating the light into a beam or a cone, as desired, before transmitting the light into gas 70, and photodiode light detector 82 may include an integral collecting lens for collecting scattered light from the gas 70 over a desired cone. A purge gas supply 84 is provided adjacent the emitter 80 and the detector 82 to periodically emit gas, such as air, to clean the devices 80 and 82. Controller 23 controls the operation of the devices 80, 84 and 82 and receives the signals from the detector 82.

The controller 23 may be integrated into the controller of a vehicle, for example, and thus the signals from light detector 82 may be used by the controller 23 to modify or control other operations of the vehicle.

The amount of particulate measured in the exhaust stream by the system can be used for diagnosis or control of engines and exhaust systems. For instance, assume one cylinder of a multicylinder diesel engine is emitting higher particulate levels than the other cylinders, and that the detector 82 or 40 has generated a signal indicating that fact. Based on the signals from the detector 82 or 40, the controller 24 may calculate information on the higher particulate amount and may calculate new operation parameters for the engine to correct the higher particulate amount. For example controller 24 may alter the fuel injection parameters for that cylinder on subsequent combustion cycles for the purpose of reducing particulate emissions of that cylinder to acceptable levels. Common fuel injection parameters of interest are the number of fuel injection events per engine cycle, the amount of fuel injected per event, and the timing of the each fuel injection event relative to cylinder position. These parameters can be adjusted by controller 24 to reduce particulate emissions while maintaining required power output and fuel efficiency. Similarly, other controls may be used to control particulate emissions from combustion such as combustion swirl actuators, intake throttle and valve actuation, turbocharger speed, etc.

Another example showing feedback control by controller 24 is the control of emission control devices. A diesel particulate filter is commonly used for collecting and oxidizing or burning particulate matter to reduce tailpipe particulate emissions to regulated levels. The filter operates by storing particulate during normal operation; then, after a certain level of particulate has accumulated on the filter, the filter temperature is increased to approximately 500-700° C. to oxidize the stored particulate and clean the filter for subsequent particulate storage. The heating and cleaning of the filter is commonly called "regeneration". Since heating the filter to temperatures suitable for regeneration requires energy and may impact engine performance, accurate tracking of the amount of particulate on the filter is desired. The particulate sensors described here, particularly detectors 46a or detector 82 can be placed for detecting upstream of the diesel particulate filter in the exhaust system to monitor and integrate particulate levels in the exhaust to track the amount of particulate stored on the filter based on the filter efficiency which is generally very high (~99%). The data may be used by controller 23 to more accurately determine when the diesel particulate filter should be regenerated; thus, active control can potentially reduce regeneration frequency which improves fuel efficiency and lessens the impact on engine operation. Similarly, a particulate sensor (eg. detector 82 or 46a) could be placed for detection downstream of the diesel particulate filter to detect threshold particulate levels to enable diagnosis by controller 23 of filter failure which would lead to higher particulate tailpipe emissions. The controller 23 could signal failure of the filter by turning on warning lights or could initiate procedures to repair the failed filter, such as regeneration procedures described above.

The foregoing descriptions of embodiments have been presented for purposes of illustration and exposition. They are not intended to be exhaustive or to limit the embodiments to the precise forms disclosed. Obvious modifications or variations are possible in light of the above teachings. The embodiments are chosen and described in an effort to provide the best illustrations of principles and practical applications, and to thereby enable one of ordinary skill in the art to utilize the various embodiments as described and with various modifications as are suited to the particular use contemplated. All such modifications and variations are within the scope of the appended claims when interpreted in accordance with the breadth to which they are fairly, legally, and equitably entitled.

What is claimed is:

1. A system for sensing exhaust particulate in a combustion exhaust gas stream comprising:
   an exhaust conduit for directing the combustion exhaust gas stream;
   a light transmitting system having a source of light in communication with a light transmitter positioned proximate the exhaust conduit and in fluid communication with the combustion exhaust gas stream for transmitting light into the combustion exhaust gas;
   a light detection system having a light detector in communication with a light collector positioned proximate the exhaust conduit and in fluid communication with the combustion exhaust gas stream for detecting a portion of the transmitted light scattered by the particulate; and
   a controller operatively associated with said light transmitting system and said light detection system for sending command signals to the source of light and monitoring signals generated by said light detection system to measure an amount of particulate matter in the combustion exhaust gas stream.

2. The system of claim 1, further comprising:
   a purge gas system for directing a flow of gas proximate the light transmitter and the light collector;
   an aperture in the exhaust conduit; and
   a cylinder having an open exit end disposed in the aperture in the exhaust conduit, wherein the light transmitter and the light collector and the purge gas system terminate at a substantially common longitudinal location of the cylinder.

3. The system of claim 2, wherein the controller is operatively associated with said purge gas system and controls a flow of purge gas.

4. The system of claim 2 wherein the purge gas system provides the purge gas at a pressure of 20 psi at a flow rate of from 5 to 10 slpm proximate the light transmitter and the light collector.

5. The system of claim 1, further comprising a bandpass filter disposed between the light collector and the light detector, the bandpass filter configured to pass only light of a wavelength emitted by the light transmitter.

6. The system of claim 1, wherein the exhaust conduit is located either upstream or downstream of an emission control device.

7. The system of claim 1, wherein the light collector is disposed adjacent the light transmitter for detecting a portion of the transmitted light back-scattered by the particulate in a direction toward the light transmitter.

8. The system of claim 1 wherein the light transmitting system comprises a plurality of light transmitters having an overlapping zone of transmitted light.

9. The system of claim 1, wherein the controller monitors the signal generated by the detector as a function of time.

10. The system of claim 1, wherein the controller monitors the signal generated by the detector as a function of a combustion cycle.

11. The system of claim 1, wherein the controller monitors the signal generated by the detector as a function of a cylinder crank angle.

12. The system of claim 1 further comprising:
    an aperture in the exhaust conduit;
    a cylinder having an open exit end disposed in the aperture in the exhaust conduit, wherein the light transmitter and the light collector terminate at a substantially common longitudinal location of the cylinder.

13. The system of claim 1 wherein the light transmitter transmits the transmitted light in a conical transmission region and the light detector detects the portion of the transmitted light from a conical detection region that overlaps the conical transmission region.

14. A method of sensing an amount of particulate matter in a stream of combustion exhaust gas disposed in a conduit, the method comprising the steps of:
    transmitting light in a conical transmission region from a light source through a first light transmitting conduit disposed in a cylinder having an open exit end disposed in an aperture in the conduit into the stream of combustion exhaust gas;
    collecting a portion of the transmitted light scattered by particulate matter entrained in the combustion exhaust gas from a conical detection region with a second light transmitting conduit disposed in the cylinder, wherein the first light transmitting conduit and the second light transmitting conduit both occur at a substantially common longitudinal location of the cylinder and wherein the conical detection region overlaps the conical transmission region;
    directing the scattered light portion of transmitted light to a light detector through the second light transmitting conduit; and
    monitoring signals generated by the light detector to measure the amount of particulate matter in the stream of combustion exhaust gas.

15. The method of claim 14, further comprising the step of introducing purge gas at the substantially common longitudinal location of the cylinder and between the light transmitting conduits and the combustion exhaust gas stream for cleaning the light transmitting and detection components.

16. The method of claim 15 wherein the step of introducing purge gas between the light transmitting conduits and the combustion gas stream comprises introducing the purge gas at a pressure of 20 psi at a flow rate of from 5 to 10 slpm.

17. The method of claim 14, further comprising the step of using the monitored signals to control operation of a device that is generating the combustion exhaust gas stream.

18. The method of claim 14 further comprising the step of controlling the emissions of at least one cylinder of an internal combustion engine by calculating new operational parameters for the at least one cylinder based on the measured amount of particulate matter in the combustion exhaust gas stream.

19. The method of claim 14 further comprising the step of using the monitored signals to control the operation of an emission control device.

20. The method of claim 14 further comprising the step of using the measured amount of particulate matter in the combustion exhaust gas stream to control a timing of a regeneration cycle of a particulate filter whereby the filter is periodically cleaned by regeneration.

21. The method of claim 14, further comprising the step of using the monitored signals to detect threshold increases in particulate matter that would signal malfunction of a device that is generating the combustion exhaust gas stream.

22. The method of claim 14, wherein the providing, collecting, directing and monitoring steps are each repeated for multiple combustion exhaust gas streams, and further comprising the step of multiplexing the multiple signals generated by the detectors to measure the amounts of particulate matters in the multiple streams of combustion exhaust gases.

23. The method of claim 14, wherein collecting a portion of the transmitted light source scattered by particulate matter entrained in the combustion exhaust gas comprises collecting a portion of the transmitted light source back-scattered by the particulate matter.

24. The method of claim 14 further comprising transmitting light through a plurality of first transmitting conduits to form an overlapping zone of transmitted light.

25. The method of claim 14, wherein monitoring signals generated by the detector comprises monitoring the signals as a function of time.

26. The method of claim 14, wherein monitoring signals generated by the detector comprises monitoring the signals as a function of a combustion cycle.

27. The method of claim 14, wherein monitoring signals generated by the detector comprises monitoring the signals as a function of a cylinder crank angle.

* * * * *